(12) United States Patent
Lee et al.

(10) Patent No.: US 10,102,349 B2
(45) Date of Patent: Oct. 16, 2018

(54) MOLECULAR ORBITAL SIMILARITY DEVIATION EVALUATION METHOD, AND SYSTEM USING SAME

(71) Applicant: LG CHEM, LTD., Seoul (KR)

(72) Inventors: Seungyup Lee, Daejeon (KR); Hyesung Cho, Daejeon (KR)

(73) Assignee: LG Chem, Ltd., Seoul (KR)

( * ) Notice: Subject to any disclaimer, the term of this patent is extended or adjusted under 35 U.S.C. 154(b) by 346 days.

(21) Appl. No.: 14/904,651

(22) PCT Filed: Jul. 15, 2014

(86) PCT No.: PCT/KR2014/006364
§ 371 (c)(1),
(2) Date: Jan. 12, 2016

(87) PCT Pub. No.: WO2015/009016
PCT Pub. Date: Jan. 22, 2015

(65) Prior Publication Data
US 2016/0171182 A1    Jun. 16, 2016

(30) Foreign Application Priority Data

Jul. 15, 2013 (KR) .................. 10-2013-0082930

(51) Int. Cl.
*G06F 19/00* (2018.01)
(52) U.S. Cl.
CPC .................. *G06F 19/701* (2013.01)
(58) Field of Classification Search
CPC .................................................. G06F 19/701
See application file for complete search history.

(56) References Cited

U.S. PATENT DOCUMENTS

| 7,570,055 B1 | 8/2009 | Clougherty et al. |
| 2007/0043545 A1* | 2/2007 | Yonezawa ............. G06F 19/701 703/11 |

(Continued)

FOREIGN PATENT DOCUMENTS

| JP | 6-332880 A | 12/1994 |
| JP | 2011-173821 A | 9/2011 |

OTHER PUBLICATIONS

Zhang et al., "Comparison of DFT Methods for Molecular Orbital Eigenvalue Calculations", J. Phys. Chem. A, Feb. 2007, 111, pp. 1554-1561.*

(Continued)

*Primary Examiner* — Cory W Eskridge
(74) *Attorney, Agent, or Firm* — Dentons US LLP

(57) ABSTRACT

The present invention relates to a molecular orbital similarity deviation evaluation method comprising: a) a step for selecting two subject molecular orbitals, the molecular orbital similarity of which is to be compared, then obtaining $N_x$ multi-block spectrums (MBS) having different block sizes, and subsequently combining $N_x$ MBS pairs having the same block size; b) a step for calculating a TSS(m) score for each MBS pair (m being the number of the MBS and being from 1 to $N_x$) by carrying out a multi-step uniformity evaluation on the $N_x$ MBS pairs; and c) a step for calculating the standard deviation of the TSS(m) scores for the $N_x$ MBS pairs and using same to quantitatively evaluate the molecular orbital similarity deviation.

13 Claims, 2 Drawing Sheets

(56) References Cited

U.S. PATENT DOCUMENTS

| | | | |
|---|---|---|---|
| 2008/0059549 A1 | 3/2008 | Aoki et al. | |
| 2010/0082306 A1* | 4/2010 | Mills | G06F 19/701 703/2 |
| 2011/0066414 A1* | 3/2011 | Mills | G06F 19/701 703/11 |
| 2011/0253991 A1 | 10/2011 | Oyamada et al. | |
| 2012/0185513 A1 | 7/2012 | Samukawa | |
| 2013/0262054 A1* | 10/2013 | Matsuura | G06F 19/701 703/2 |
| 2014/0172387 A1* | 6/2014 | Ford | G06F 19/704 703/2 |
| 2015/0051882 A1* | 2/2015 | Canfield | A01K 67/033 703/2 |
| 2015/0142398 A1* | 5/2015 | Miller, III | G06F 19/701 703/2 |
| 2016/0078155 A1* | 3/2016 | Mochizuki | G06F 19/16 703/2 |
| 2016/0140325 A1* | 5/2016 | Lee | G06F 19/701 703/2 |
| 2016/0162663 A1* | 6/2016 | Lee | G06F 19/701 702/32 |
| 2016/0371467 A1* | 12/2016 | Lee | G06F 19/701 |
| 2016/0378910 A1* | 12/2016 | Olson | G06F 19/701 703/2 |
| 2016/0378955 A1* | 12/2016 | Lee | G06F 19/701 702/23 |

OTHER PUBLICATIONS

Miessler et al., Chapter 5 of "Organic Chemistry, 5th Edition", Dec. 1999, 52 pages.*

Mireia Guell et al., "Analysis of Electron Delocalization in Aromatic Systems: Individual Molecular Orbital Contributions to Para-Delocalization Indexes", J. Phys. Chem. A., 2006, 110, pp. 11569-11574.

* cited by examiner

MOLECULAR ORBITAL SIMILARITY DEVIATION EVALUATION METHOD, AND SYSTEM USING SAME

This application is a National Stage Application of International Application No. PCT/KR2014/006364, filed on Jul. 15, 2014, which claims the benefit of Korean Patent Application No. 10-2013-0082930, filed on Jul. 15, 2013, all of which are hereby incorporated by reference in their entirety for all purposes as if fully set forth herein.

TECHNICAL FIELD

The present disclosure relates to a method for evaluating similarity deviation between molecular orbitals, and to a system using the same. More particularly, the present disclosure relates to a method for precisely evaluating similarity deviation between molecular orbitals in a quantitative manner, and to a system using the same.

BACKGROUND ART

Electrochemical properties of a material are greatly influenced by the behavior of electrons therein. Because the behavior of electrons in a molecule is very complex and difficult to analyze, it cannot be directly evaluated by experiments. In practice, the behavior of an electron is analyzed by computation rather than by experiments, and the concept of a molecular orbital (MO) is used to simulate the behavior of an electron.

Molecular orbitals, which account for the distributions of electrons in a specific region in a molecular structure as a probability concept, cannot be obtained experimentally, but can be constructed using quantum mechanics. Typically, the evaluation of molecular orbitals depends on a qualitative approach in which computed molecular orbitals are depicted as diagrams and visually evaluated. Though useful as a qualitative method to roughly evaluate the entire properties of molecular orbitals, such a method cannot analyze molecular orbitals precisely and objectively. When such a qualitative method is employed, the evaluation of the same molecule may differ from one evaluator to another because the evaluation criterion is absolutely subjective.

In order to surmount problems with such qualitative evaluation methods, the present inventors developed various methods for quantitatively analyzing a molecular orbital by which molecular orbital information can be systematically and precisely evaluated.

For example, there are an infinite number of molecular orbital distribution patterns that may exist in an entire molecular structure. A new block concept was introduced to intuitively and correctively evaluate such complex molecular orbital distribution patterns. A method based on the block concept is designated AC2B (Assembly of Consecutive Building Block).

In the AC2B method, (1) the entire molecular structure of a molecule is divided into blocks, and (2) ratios of molecular orbitals associated with individual blocks to a sum of the entire molecular orbital are calculated, followed by rearranging the blocks consecutively on the basis of the calculated ratios to give a rearranged consecutive block spectrum that accounts for molecular orbital properties. In the rearranged consecutive block spectrum, the first block is responsible for the greatest distribution of the molecular orbital whereas the last block confines the smallest distribution of the molecular orbital. The AC2B method in which advantage is taken of a new block concept can simplify the complex molecular orbital distribution patterns and allows for the precise evaluation of molecular orbital properties in an intuitive manner.

However, the rearranged block spectra created through AC2B intuitively enables the analysis of molecular orbital properties of individual molecules, but cannot be directly applied to the comparison of molecular orbitals between different molecules. This is because the block spectra are consecutive arrangements of blocks according to the ratio size so that they cannot be directly used in quantitative comparison between different molecular orbitals.

The present inventors, therefore, developed a 2BS-score method for determining similarity between different molecular orbitals on the basis of the block spectrum method in which a novel block concept is introduced to precisely express various and complex molecular orbital distribution patterns in an intuitive manner.

The 2BS-score method is designed to quantitatively analyze similarity between two different molecular orbitals by comparing block spectra calculated for the different molecular orbitals. In the 2BS-score method, block spectra of molecular orbitals of interest are compared in a three-step manner to analyze similarity between molecular orbitals. For example, when block spectra of two molecular orbitals to be compared are identical, the 2BS-score is 100%. A larger sequence deviation between block spectra gives a smaller 2BS-score value, which explains poorer similarity between the molecular orbitals. Thus, the 2BS-score method can precisely determine molecular orbital similarity in a quantitative manner.

However, the 2BS-score, although able to quantitatively evaluate molecular orbital similarity, does not provide information on the degree of the similarity deviation. For example, when the two molecular orbital pairs A0-A1 and A2-A3 are evaluated for similarity using 2BS-score, the same 2BS-score values given to the two pairs indicate the same similarity therebetween. In practice, however, similarity between A0-A1 is not identical to that between A2-A3 because there exists a deviation in similarities that A0-A1 and A2-A3 have even at the same 2BS-score values.

Precise measurement of such a similarity deviation would more accurately evaluate similarity between molecular orbitals, and thus could be useful for understanding similarity properties. According to this necessity, the present inventors developed a novel method for statistically evaluating similarity deviation, which is a new property of similarity between molecular orbitals, by quantitatively analyzing similarity between molecular orbitals according to 2BS-score.

DISCLOSURE

Technical Problem

Accordingly, the present invention has been made keeping in mind the above problems occurring in the prior art, and an object of the present disclosure is to provide a novel method for precisely evaluating similarity deviation of molecular orbitals in a quantitative manner.

Technical Solution

The present disclosure addresses a method for evaluating similarity deviation between molecular orbitals, comprising: a) selecting two molecular orbitals to be compared for molecular orbital similarity, and obtaining $N_x$ MBS pairs by i) computing molecular orbital distributions by a quantum chemistry calculation, ii) building N blocks arranged in a radial direction from the center of the molecular structure, iii) calculating a molecular orbital ratio (BX(k)) associated with each of the blocks (k is a natural number and represents a block number ranging from 1 to N), iv) rearranging the blocks consecutively by orbital ratio (BX(k)) size, v) with the exception that blocks are built at different sizes, repeating steps ii) to iv) for the individual molecular orbitals of interest to give $N_x$ MBS (multi-block spectra) per molecular orbital, the MBS being different in block size, and assembling $N_x$ MBS pairs by block size; b) performing multi-step identity estimation on the $N_x$ MBS pairs to calculate TSS(m) for each of the MBS pairs (m is an MBS number ranging from 1 to $N_x$); and c) calculating a standard deviation of TSS (m) for each of the MBS pairs, and evaluating similarity deviation between molecular orbitals on the basis of the calculated deviations.

Advantageous Effects

As described above, the method in accordance with the present disclosure allows for the exact evaluation of similarity deviation between molecular orbitals and thus can comprehensively evaluate and understand properties associated with molecular orbital similarity, which is useful in developing novel materials for OLEDs (organic light-emitting diodes) or solar cells.

BEST MODE

Below, a detailed description will be given of the present invention.

The present disclosure addresses a method for evaluating similarity deviation between molecular orbitals, comprising: a) selecting two molecular orbitals to be compared for molecular orbital similarity, and obtaining $N_x$ MBS pairs by i) computing molecular orbital distributions by a quantum chemistry calculation, ii) building N blocks arranged in a radial direction from the center of the molecular structure, iii) calculating a molecular orbital ratio (BX(k)) associated with each of the blocks (k is a natural number and represents a block number ranging from 1 to N), iv) rearranging the blocks consecutively by orbital ratio (BX(k)) size, v) with the exception that blocks are built at different sizes, repeating steps ii) to iv) for the individual molecular orbitals of interest to give $N_x$ MBS (multi-block spectra) per molecular orbital, the MBS being different in block size, and assembling $N_x$ MBS pairs by block size; b) performing a multi-step identity estimation on the $N_x$ MBS pairs to calculate TSS(m) for each of the MBS pairs (m is an MBS number ranging from 1 to $N_x$); and c) calculating a standard deviation of TSS (m) for each of the MBS pairs, and evaluating similarity deviation between molecular orbitals on the basis of the calculated deviations.

Figure 1:
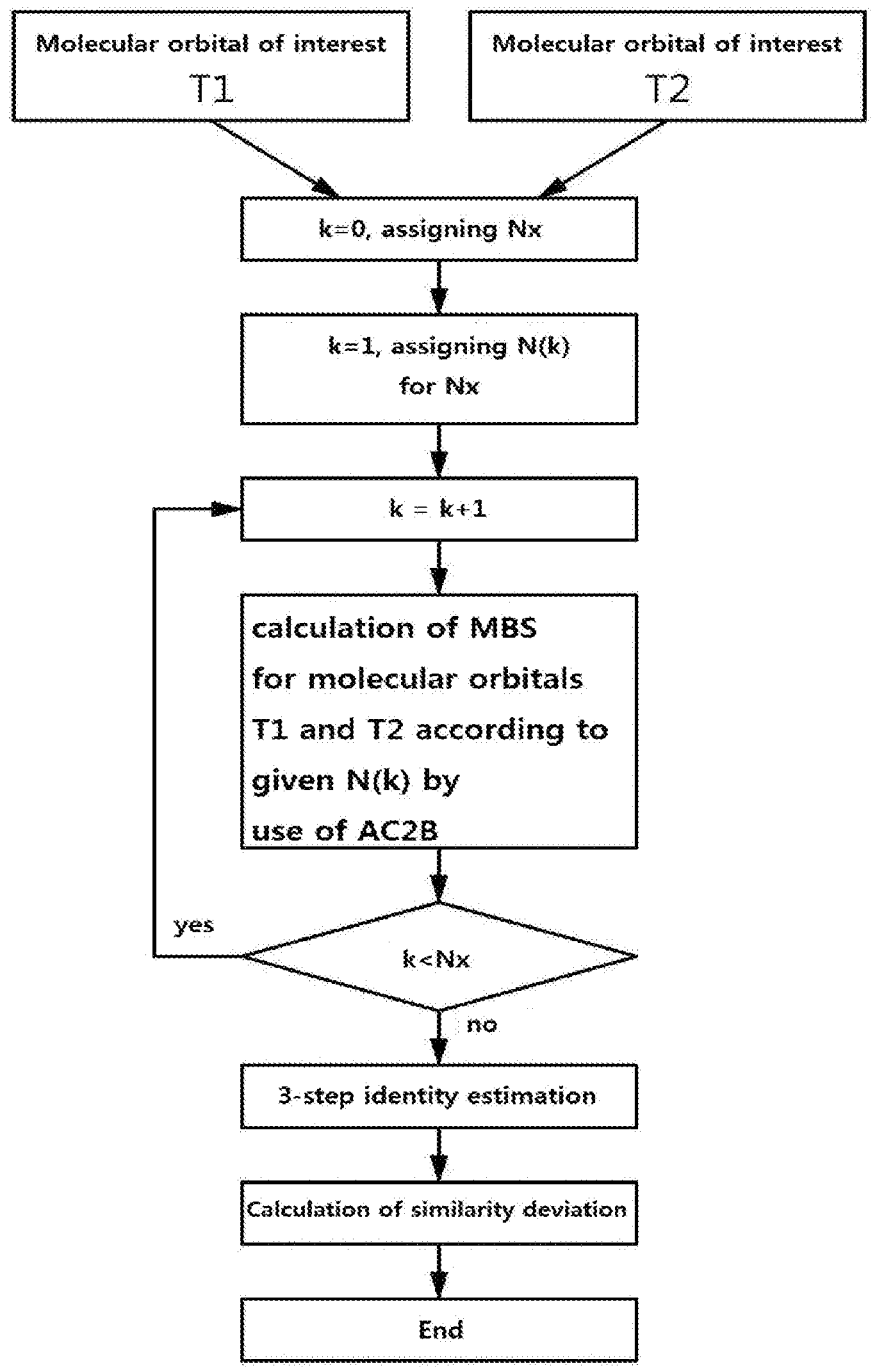
FIG. 1 is a flow chart illustrating an evaluation procedure of similarity deviation between molecular orbitals in accordance with an embodiment of the present disclosure.

In the present disclosure, the method for evaluating similarity deviation between molecular orbitals is designated "SDE-MO (Statistical Similarity Deviation Estimation-Molecular Orbital)". The SSDE-MO method is adapted to quantitatively calculate a similarity deviation between molecular orbitals through statistical estimation. In the SSDE-MO method, a similarity deviation between different molecular orbitals is calculated by (1) creating N MBS (Multi-level Block Spectra) that are different in block size, (2) evaluating the MBS of each pair for identity to calculate similarity of the molecular orbitals in each MBS pair, and (3) statistically calculating similarity deviation based on the data of similarity in each MBS pair. FIG. 1 is a flow chart illustrating the calculation procedure of SSDE-MO. The calculation procedure of SSDE-MO will be described in detail with reference to FIG. 1.

First, the method of the present disclosure proceeds with a) selecting two molecular orbitals to be compared for molecular orbital similarity, and obtaining $N_x$ MBS pairs by i) computing molecular orbital distributions by a quantum chemistry calculation, ii) building N blocks arranged in a radial direction from the center of the molecular structure, iii) calculating a molecular orbital ratio (BX(k)) associated with each of the blocks (k is a natural number and represents a block number ranging from 1 to N), iv) rearranging the blocks consecutively by orbital ratio (BX(k)) size, v) with the exception that blocks are built at different sizes, repeating steps ii) to iv) for the individual molecular orbitals of interest to give $N_x$ MBS (multi-block spectra) per molecular orbital, the MBS being different in block size, and assembling $N_x$ MBS pairs by block size.

In step a), "AC2B (Assembly of Consecutive Building Block)", which is a method developed by the present inventors for analyzing a molecular orbital property, is employed.

A molecular orbital is defined as a mathematical function describing the wave-like behavior of an electron in a molecule. Regions in which molecular orbitals exist can be obtained by a quantum-mechanical calculation. Any calculation method that takes advantage of quantum mechanics may be employed without limitations to obtain molecular orbital distributions. Preferable may be calculation through the distribution of the electron density function ($\psi^2$), which is a square of the orbital wave function ($\psi$) in each point determined in a molecular structure, or through single-point energy calculation or geometry optimization calculation. The present inventors calculated molecular orbital distributions using the program MATERIAL STUDIO DMol3 (ACCELRYS), which uses the Density Functional Theory (DFT), and depicted molecular orbital diagrams using the program VISUALIZER from MATERIAL STUDIO.

According to the present disclosure, the entire molecular structure of a molecule to be analyzed for molecular orbital properties is composed of an assembly of N consecutive blocks created in a radial direction from the center of the molecule over the entire molecular structure.

In this regard, the greatest RDM (Radially Discrete Mesh) that covers the entire molecular structure in a radial direction with a starting point at the center of the molecule (r=0.0) is calculated, and its size is designated r=1.0. RDM is a concept of confining the elemental atoms of a molecular structure within meshes arranged in a radial direction from the center of a molecule. In the molecular structure calculation through RDM, an intramolecular center ($x_c$, $y_c$, $z_c$) is obtained according to the following Mathematical Formulas 1-1 to 1-3.

$$x_C = \frac{1}{N^{Coord}} \sum_{k=1}^{N^{Coord}} x_K \qquad \text{(Math Formula 1-1)}$$

$$y_C = \frac{1}{N^{Coord}} \sum_{k=1}^{N^{Coord}} y_K \qquad \text{(Math Formula 1-2)}$$

$$z_C = \frac{1}{N^{Coord}} \sum_{k=1}^{N^{Coord}} z_K \qquad \text{(Math Formula 1-3)}$$

wherein $N^{Coord}$ represents the total number of atomic coordinates constituting a molecule.

The total number of blocks, N, is not particularly limited, but preferably ranges from 3 to 100.

According to the molecular structure calculation by RDM, the entire molecular structure of a molecule of interest can be divided into blocks on the basis of distance from the center of the molecule.

Step a) may comprise calculating a molecular orbital ratio (BX(k)) associated with each of the blocks.

By the term "orbital ratio (BX(k)) associated with each of the blocks" is meant an amount that a molecular orbital associated with a $k^{th}$ block occupies in comparison with the sum of entire molecular orbitals. The orbital ratio (BX(k)) associated with each of the blocks can be obtained by calculating individual molecular orbitals BMO(k)) associated with individual blocks, calculating a total sum of the entire molecular orbital from the individual molecular orbitals, and dividing the individual molecular orbitals BMO(k)) associated with each of the blocks by a total sum of the entre molecular orbital.

Also, step a) may comprise rearranging the blocks consecutively by size of the orbital ratio (BX(k)) to give a rearranged block spectrum. As used herein, the term "rearranged block spectrum" refers to AC2B (Assembly of Consecutive Building Block) obtained by rearranging the blocks built in step a) consecutively by the size of BX(k).

To obtain $N_x$ MBS (multi-block spectra) different in block size from each other, sub-steps ii) to iv) are repeated for the individual molecular orbitals of interest, with the exception that blocks are built at different sizes, in step a). Information about changes in similarity between molecular orbitals under various conditions is necessary for statistically estimating similarity deviation between molecular orbitals. To this end, $N_x$ (=total number of blocks) MBS for each molecular orbital, different in block size from each other, is created. The molecular orbitals to be compared are designated T1 and T2, respectively. In AC2B, the default number of blocks for generating a BS (block spectrum) is 5. In order to create MBS, $N_x$, which is the total number of MBS, and N(k), which is a set of blocks according to size, must be predetermined. $N_x$ should be greater than 1, and may vary depending on the efficiency of calculation and the purpose of use. By way of example, when $N_x=6$, the block size set may be established as follows.

N={5,6,7,8,9,10}

Sub-steps ii)~iv) are repeated according to block size to obtain $N_x$ MBS (multi-block spectra), different in block size, for each of the molecular orbitals of interest.

From the $N_x$ MBS (multi-block spectra), $N_x$ MBS pairs of the same block size are assembled.

As used herein, "MBS pair" means a pair of block spectra, identical in block size, combined from the $N_x$ MBS (multi-block spectra) for each of the molecular orbitals of interest.

In this example, a total of 6 pairs of MBS, different in block size to each other, can be combined.

Also, the method of the present disclosure proceeds with b) performing a multi-step identity estimation on the $N_x$ MBS pairs to calculate TSS(m) for each of the MBS pairs (m is an MBS number ranging from 1 to $N_x$).

The multi-step identity assay of step b) may be conducted in a total of three steps for estimating the $N_x$ MBS pairs for similarity. In all of the multi-step procedure, the identity assay is performed on the basis of the comparison of the same sequences of MBS pairs. The three-step procedure will be elucidated as follows.

<First-Step Identity Estimation>

A first identity estimation is carried out through the following sequence comparison for a total of $N_x$ MBS pairs.

```
DO m=1, N_X
  DO n=1, N{m}
    IF (MBS1{m, n}=MBS2{m, n})
      IF(m eq 1)
        SC{m, n}=X if n=1
        SC{m, n}=Y if n=2
        SC{m, n}=Z if n>2
      ELSE
        SC{m, n}=0.4−0.1x(n−1) if 1≤n<N{1}
        SC{m, n}=0.0            if n≥N{1}
      END
    ELSE
      SC{m, n}=0.0
    END
  END
END
```

MBS1{m,n} abd MBS2{m,n} represent identity of blocks at position n in the MBS having a block size of N{m} created for the molecular orbitals T1 and T2, respectively.

SC{m,n} represents a degree of identity for an MBS pair having an N{m} size at position n. Through the procedure, primary identity at an MBS sequence position is estimated.

X is between 0 (zero) and 0.6 (exclusive of zero, inclusive of 0.6), Y is between 0 and 0.5 (exclusive of 0, inclusive of 0.5), and Z ranges from 0 to 0.3, with the proviso of X+Y+(N−2)×Z=1.0.

In the first identity estimation, when the block spectrum sequences of each of the $N_x$ MBS pairs are compared at the same sequence positions, SC (m, n) is assigned to the same blocks, with lower SC (m, n) values at higher n.

In the first identity estimation, when m is 1, SC(m, n)=X is assigned to the same blocks at n=1, SC(m, n)=Y to the same blocks at l=2, and SC(m, n)=Z to the same blocks at l>2. X is between 0 (zero) and 0.6 (exclusive of zero, inclusive of 0.6), Y is between 0 and 0.5 (exclusive of 0, inclusive of 0.5), and Z ranges from 0 to 0.3, with the proviso of X+Y+(N−2)×Z=1.0.

Through such procedures, primary identity at an MBS sequence position is estimated.

<Second-Step Identity Estimation>

A second identity estimation is carried out for MBS pairs as follows. Among the MBS sequences, blocks arranged at $1^{st}$ and $2^{nd}$ positions are of the highest priority because the most abundant molecular orbitals exist therein. In consideration of this situation, secondary identity estimation is carried out.

```
DO m=1, N_X
DO n=1, N{m}
    IF (MBS1{m, n}=MBS2{m, n+1} and MBS1{m,
      n+1}=MBS2{m, n})
        IF(m eq 1)
            SC{m, n}=0.4 & SC{m, n+1}=0.3        if n=1
            SC{m, n}=0.15 & SC{m, n+1}=0.05      if n=2
        ELSE
            SC{m, n}=0.32 & SC{m, n+1}=0.24      if n=1
            SC{m, n}=0.15 & SC{m, n+1}=0.1       if n=2
        END
    END
END
END
```

The second-step identity estimation comprises i) assigning a SC(m, n) value if the following condition is met: of the block spectra for each of the $N_x$ MBS pairs, a block at n=1 in a first block spectrum is identical to that at n=2 in a second block spectrum, and a block at n=2 in the first block spectrum is identical to that at n=1 in the second block spectrum; and ii) assigning a SC(m,n) value if the following condition is met: a block at n=2 in the first block spectrum is identical to that at n=3 in the second block spectrum, and a block at n=3 in the first block spectrum is identical to that at n=2 in the second block spectrum, the SC(m, n) values assigned in step i) being greater than that assigned in step ii).

<Third-Step Identity Estimation>

```
DO m=1, N_X
DO n=1, N{m}
    IF (d_BL{m, n} eq 1)
        IF(m eq 1)
            SC{m, n}=0.4              if n=1
            SC{m, n}=0.15             if n=2
            SC{m, n}=0.05             if n>2
        ELSE
            SC{m, n}=0.4              if n=1
            SC{m, n}=0.15             if n=2
            SC{m, n}=0.1-0.05x(n-3)   if 2<n<N{1}
        END
    END
END
END
```

At the same sequence position for each of the MBS pairs, a block distance (d_BL{m,n}) is calculated. That is, d_BL{m,n} is a cross distance between blocks at position n in a block spectrum having an N{m} size. For example, if MBS1{1,1}=BL5 and MBS2{1,1}=BL4 in the MBS pair having the block size N{1}, d_BL{1,1}=5−4=1. Like this, a tertiary identity estimation is carried out using the following algorithm.

In the third-step identity estimation, a criterion for a block sequence distance (d_BL{m,n}) at the same sequence position for each of the MBS pairs is established, and if a block sequence distance at each position is identical to the block sequence distance (d_BL{1}) criterion, a SC(m, n) value is assigned, with the proviso that the SC(m, n) value decreases with an increase in n.

In step b), such a multi-step identity estimation is performed on the $N_x$ MBS pairs to calculate similarity (TSS, total similarity score) for each of the MBS pairs according to the following Mathematical Formula 1.

$$TSS\{m\} = \left(\sum_{n=1}^{N\{m\}} SC\{m, n\}\right) \times 100(\%) \quad \text{[Math Formula 1]}$$

Wherein m is an MBS number ranging from 1 to $N_x$.

TSS{m} represents a degree of identity for an MBS pair at a block size of N{m}. When the orbitals in an MBS pair are identical to each other, TSS is 100%. Lower similarity is accounted for by a smaller value of TSS.

In addition, the method of the present disclosure proceeds with c) calculating a standard deviation of TSS (m) for each of the MBS pairs, and evaluating similarity deviation between molecular orbitals on the basis of the calculated deviations.

A standard deviation is calculated for $N_x$ TSS. Covering the entire MBS, the standard deviation accounts for similarity deviation between molecular orbitals. The standard deviation is larger than 0 (zero). When all TSS(m) are the same, that is, when the standard deviation of TSS(m) is 0, there is no similarity deviation between molecular orbitals. A larger standard deviation means a larger similarity deviation between molecular orbitals. By means of the standard deviation, similarity deviation between molecular orbitals can be quantitatively analyzed.

Also, the present disclosure addresses a system for evaluating similarity deviation between molecular orbitals, using the method.

The system for evaluating similarity deviation between molecular orbitals comprises:

a) a blocking module for selecting two molecular orbitals to be compared for molecular orbital similarity, and obtaining $N_x$ MBS pairs by i) computing molecular orbital distributions by a quantum chemistry calculation, ii) building N blocks arranged in a radial direction from the center of the molecular structure, iii) calculating a molecular orbital ratio (BX(k)) associated with each of the blocks (k is a natural number and represents a block number ranging from 1 to N), iv) rearranging the blocks consecutively by orbital ratio (BX(k)) size, v) with the exception that blocks are built at different sizes, repeating steps ii) to iv) for the individual molecular orbitals of interest to give $N_x$ MBS (multi-block spectra) per molecular orbital, the MBS being different in block size, b) a data input module for assembling $N_x$ MBS pairs by block size from the $N_x$ MBS (multi-block spectra) of each of the two molecular orbitals of interest, performing a multi-step identity estimation on the $N_x$ MBS pairs to calculate TSS(m) for each of the MBS pairs, and inputting the calculated data; and c) an evaluation module for calculating a standard deviation of TSS (m) for each of the MBS pairs, and evaluating similarity deviation between molecular orbitals on the basis of the calculated deviations. As used herein, the term "module" means a unit in which a certain function or action is processed, and may be embodied by hardware or software or a combination of hardware and software.

Mode for Invention

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

EXAMPLE

Figure 2:
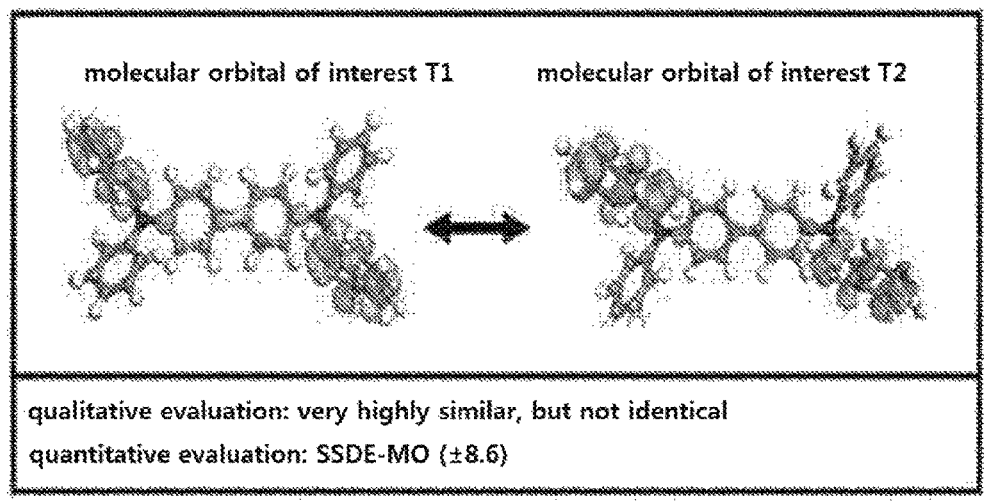
FIG. 2 is a diagram of a pair of molecular orbitals T1 and T2 for different electron states of NPB (N,N'-Di[(1-naphthyl)-N,N'-diphenyl]-1,1'-(biphenyl)-4,4'-diamine), with a deviation of ±8.6 measured by SSDE-MO.

A pair of molecular orbitals T1 and T2 for different electron states of NPB (N,N'-Di[(1-naphthyl)-N,N'-diphenyl]-1,1'-(biphenyl)-4,4'-diamine) were calculated using quantum mechanics, and were subjected to the SSDE-MO method of the present disclosure to afford TSS values for MBS pairs. As a result, a standard deviation of ±8.6 was obtained. This is a very small value indicating that there is little similarity deviation between molecular orbitals T1 and T2. For qualitative evaluation, molecular orbitals T1 and T2 were visualized using the program VISUALIZER from MATERIAL STUDIO, and are depicted in FIG. 2. As can be seen in FIG. 2, the molecular orbitals, although not identical, are very similar to each other. Thus, the similarity deviation between the molecular orbitals T1 and T2 is not large as demonstrated by the qualitative evaluation. Hence, the SSDE-MO method of the present disclosure is proven to precisely evaluate similarity deviation between molecular orbitals in a quantitative manner.

Figure 3:
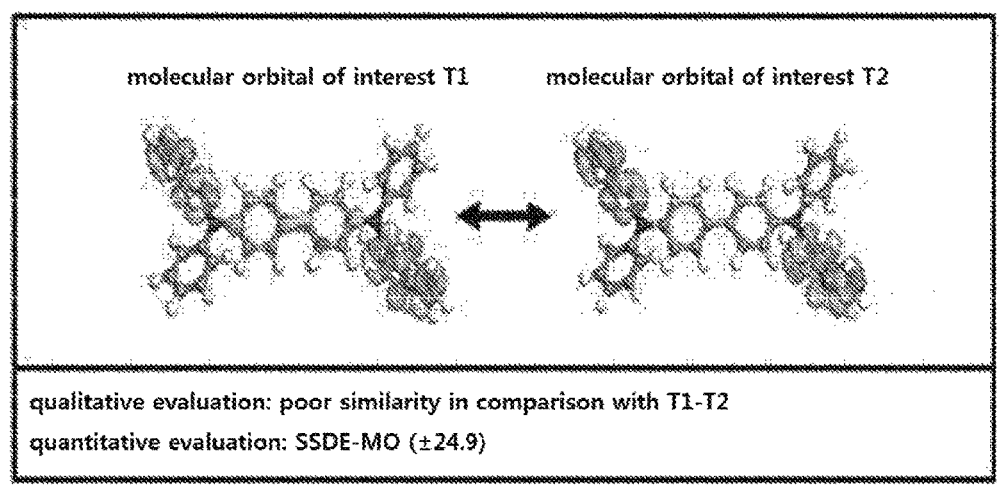
FIG. 3 is a diagram of a pair of molecular orbitals T1 and T3 for different electron states of NPB (N,N-Di[(1-naphthyl)-N,N'-diphenyl]-1,1'-(biphenyl)-4,4'-diamine), with a deviation of ±24.9 measured by SSDE-MO.

A pair of molecular orbitals T1 and T3 for different electron states of NPB (N,N'-Di[(1-naphthyl)-N,N'-diphenyl]-1,1'-(biphenyl)-4,4'-diamine) were calculated using quantum mechanics, and were subjected to the SSDE-MO method to afford TSS values for MBS pairs. As a result, a standard deviation of ±24.9 was obtained. Similarity between the molecular orbitals T1 and T3 exhibited a relatively large deviation. This quantitative SSDE-MO evaluation was exactly incident with the qualitative evaluation depicted in FIG. 3, demonstrating that the SSDE-MO method of the present disclosure can precisely evaluate similarity deviation between molecular orbitals in a quantitative manner.

The invention claimed is:

1. A method for evaluating similarity deviation between molecular orbitals of a molecular structure, comprising:
   a) selecting two molecular orbitals to be compared for molecular orbital similarity, and obtaining $N_x$ multi-block spectra (MBS) pairs by i) computing molecular orbital distributions by a quantum chemistry calculation, ii) building N blocks arranged in a radial direction from a center of the molecular structure, iii) calculating a molecular orbital ratio (BX(k)) associated with each of the blocks (k is a natural number and represents a block number ranging from 1 to N), iv) rearranging the blocks consecutively by orbital ratio (BX(k)) size, v) with an exception that blocks are built at different sizes, repeating steps ii) to iv) for individual molecular orbitals of interest to give $N_x$ MBS per molecular orbital, the MBS being different in block size, and assembling $N_x$ MBS pairs by block size;
   b) performing multi-step identity estimation on the $N_x$ MBS pairs to calculate total similarity score (TSS) (m) for each of the MBS pairs (m is an MBS number ranging from 1 to $N_x$); and
   c) calculating a standard deviation of TSS (m) for each of the MBS pairs, and evaluating similarity deviation between molecular orbitals on a basis of the calculated deviations.

2. The method of claim 1, wherein the quantum chemistry calculation of step i) is conducted through distribution of the electron density function ($\psi 2$), which is a square of the orbital wave function ($\psi$), in each point determined with regard to the molecular structure.

3. The method of claim 1, wherein the quantum chemistry calculation of step i) is conducted through single-point energy calculation or geometry optimization calculation.

4. The method of claim 1, wherein the orbital ratio (BX(k)) associated with each of the blocks in step iii) is obtained by calculating individual molecular orbitals BMO (k) associated with individual blocks, calculating a total sum of the entire molecular orbital from the individual molecular orbitals, and dividing the individual molecular orbitals BMO(k)) associated with each of the blocks by a total sum of the entre molecular orbital.

5. The method of claim 1, wherein the quantum chemistry calculation of step a) uses an RDM calculation method.

6. The method of claim 1, wherein the multi-step identity estimation is carried out in a total of three steps for estimating the $N_x$ MBS pairs for similarity.

7. The method of claim 6, wherein a first identity estimation of the three steps is carried out in such a manner that when the block spectrum sequences of each of the $N_x$ MBS pairs are compared at the same sequence positions, SC (m, n) is assigned to the same blocks, with lower SC (m, n) values at higher n (m is an MBS number ranging from 1 to N).

8. The method of claim 6, wherein the first identity estimation is carried out in such a manner that
   when m is 1, SC(m, n)=X is assigned to the same blocks at n=1, SC(m, n)=Y is assigned to the same blocks at l=2, and SC(m, n)=Z is assigned to the same blocks at l>2, and
   X is between 0 (zero) and 0.6 (exclusive of zero, inclusive of 0.6), Y is between 0 and 0.5 (exclusive of 0, inclusive of 0.5), and Z ranges from 0 to 0.3, with the proviso of X+Y+(N−2)×Z=1.0.

9. The method of claim 6, wherein a second-step identity estimation of the three steps comprises:
   i) assigning an SC(m, n) value if the following condition is met: of the block spectra for each of the $N_x$ MBS pairs, a block at n=1 in a first block spectrum is identical to that at n=2 in a second block spectrum, and a block at n=2 in the first block spectrum is identical to that at n=1 in the second block spectrum, and
   ii) assigning an SC(m,n) value if the following condition is met: a block at n=2 in the first block spectrum is identical to that at n=3 in the second block spectrum and a block at n=3 in the first block spectrum is identical to that at n=2 in the second block spectrum, the SC(m, n) values assigned in step i) being greater than that assigned in step ii).

10. The method of claim 6, wherein a third-step identity estimation of the three steps is carried out in such a manner that a criterion for a block sequence distance (d_BL{m,n}) at the same sequence position for each of the MBS pairs is established, and if a block sequence distance at each position is identical to the block sequence distance (d_BL{1}) criterion, an SC(m, n) value is assigned, with the proviso that the SC(m, n) value decreases with an increase in n.

11. The method of claim 1, wherein the TSS(m) of step b) is calculated according to the following Mathematical Formula 1:

$$TSS\{m\} = \left(\sum_{n=1}^{N\{m\}} SC\{m, n\}\right) \times 100(\%) \quad \text{[Math Formula 1]}$$

wherein m is an MB S number ranging from 1 to $N_x$.

12. The method of claim 1, wherein the similarity deviation between molecular orbitals in step c) is determined in such a manner that when the standard deviation is 0, there is no similarity deviation between molecular orbitals, and that a larger standard deviation means a larger similarity deviation between molecular orbitals.

13. A system for evaluating similarity deviation between molecular orbitals of a molecular structure, comprising:

a) a blocking module for selecting two molecular orbitals to be compared for molecular orbital similarity, and obtaining $N_X$ multi-block spectra (MBS) pairs by i) computing molecular orbital distributions by a quantum chemistry calculation, ii) building N blocks arranged in a radial direction from a center of the molecular structure, iii) calculating a molecular orbital ratio (BX(k)) associated with each of the blocks (k is a natural number and represents a block number ranging from 1 to N), iv) rearranging the blocks consecutively by orbital ratio (BX(k)) size, v) with an exception that blocks are built at different sizes, repeating steps ii) to iv) for individual molecular orbitals of interest to give $N_x$ MBS per molecular orbital, the MBS being different in block size, b) a data input module for assembling $N_x$ MBS pairs by block size from the $N_x$ MBS (multi-block spectra) of each of the two molecular orbitals of interest, performing a multi-step identity estimation on the $N_X$ MBS pairs to calculate total similarity score (TSS) (m) for each of the MBS pairs, and inputting the calculated data; and c) an evaluation module for calculating a standard deviation of TSS (m) for each of the MBS pairs, and evaluating similarity deviation between molecular orbitals on a basis of the calculated deviations.

* * * * *